US00PP11632P

United States Patent [19]

Walden

[11] Patent Number: Plant 11,632

[45] Date of Patent: Nov. 14, 2000

[54] MINIATURE ROSE PLANT NAMED 'JACNUYE'

[75] Inventor: John K. Walden, Thousand Oaks, Calif.

[73] Assignee: Bear Creek Gardens, Inc., Medford, Oreg.

[21] Appl. No.: 09/232,015

[22] Filed: Jan. 14, 1999

[51] Int. Cl.[7] ..... A01H 5/00

[52] U.S. Cl. ..... Plt./126

[58] Field of Search ..... Plt./116, 119, 122, Plt./123, 126, 129

*Primary Examiner*—Howard J. Locker

*Attorney, Agent, or Firm*—Klarquist Sparkman Campbell Leigh & Whinston, LLP

[57] ABSTRACT

A miniature rose plant having bright orange to orange-red flower color; pointed ovoid bud; small, two-inch flowers; and dark green, glossy, powdery mildew resistant foliage.

1 Drawing Sheet

The present invention relates to a new and distinct variety of rose plant of the miniature rose plant class which was originated by me by crossing the variety 'MACnewye', U.S. Plant Pat. No. 5,428, with an unnamed seedling (unnamed seedling×MORpints).

The primary objective of this breeding was to produce a new rose variety having a miniature rose plant habit; a bright orange to orange-red color; pointed ovoid bud; small flowers two inches in diameter; and dark green, glossy, disease resistant foliage. The objective was substantially achieved, along with other desirable improvements, as evidenced by the following unique combination of characteristics that are outstanding in the new variety and that distinguish it from its parents, as well as from all other varieties of which I am aware:

1. A miniature (dwarf) plant habit;
2. Pointed ovoid buds;
3. Small, two-inch flowers;
4. Bright orange-red color;
5. Dark green, glossy foliage; and
6. Resistance to powdery mildew.

Asexual reproduction of this new variety by cuttings as performed at Wasco, Calif., shows that the foregoing and all other characteristics and distinctions come true to form and are established and transmitted through suceedling propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—'MACnewye', U.S. Plant Pat. No. 5,428.

*Pollen parent*.—Unnamed seedling (unnamed seedling×MORpints).

Classification:

*Botanical*.—*Rosa hybrida*.

*Commercial*.—Miniature rose.

FLOWER

Observations made from specimens grown in a garden and greenhouse environment at Somis, Calif. on Dec. 18, 1998.

Blooming habit: Continuous.

Bud:

*Size*.—About ¾ inch long when the petals start to unfurl.

*Form*.—The bud form is short, pointed ovoid.

*Color*.—When sepals first divide, bud color is near Orange-Red Group 34A. When half blown, the upper and lower sides of the petals are near Orange-Red Group 32A.

*Sepals*.—Color: Near Yellow-Green Group 146B. Surface texture: Slightly rough and glandular. There are three lightly appendaged sepals. There are two unappendaged sepals with hairy edges.

*Receptacle*.—Color: Yellow-Green Group 144A. Shape: Apple. Size: Small, about 5/16 inch×5/16 inch. Surface: Smooth.

*Peduncle*.—Length: Short, averaging about 1½ inches. Surface: Glandular. Color: Yellow-Green Group 144A. Strength: Stiff, erect, slender.

Bloom:

*Size*.—Small. Average open size is two inches.

*Borne*.—Mostly singly and basal stems normally terminate in clusters of three to five blooms having flat, irregular shape.

*Stems*.—Normal, Average length is about seven inches.

*Form*.—When first open: Cupped. Permanence: Outer petal edges curl slightly.

*Petalage*.—Number of petals under normal conditions: 20–25.

*Color*.—The upper and reverse sides of the petals are Orange-Red Group 30A. The base of each petal has a ¼" Yellow-Group 12B crescent. The major color on the upper sides is Orange-Red Group 30A.

*Discoloration*.—The general tonality at the end of the first day: Orange-Red Group 30A. At the end of the third day: Near Orange-Red Group 32A. Color changes with further aging to Red Group 41B.

*Fragrance*.—Slight; lightly spicy.

Petals:

*Texture*.—Thick.

*Shape*.—Deltoid.

*Form*.—Tips slightly recurved.

*Arrangement*.—Imbricated. Petaloids in the center: Few (three to five), large.

*Persistence*.—Petals drop off cleanly before drying.

*Lastingness*.—On the plant: Long, about nine days. As a cut flower: Not tested.

Reproductive parts:

*Anthers*.—Size: Medium. Quantity: Many. Color: Yellow-Orange Group 17D. Arrangement: Regular around styles.

*Filaments*.—Color: Orange-Red Group 34A on distal ⅔ and Yellow-Orange Group 14B on the lower proximal ⅓.

*Pollen*.—Color: Yellow-Orange Group 22A.

*Styles*.—Color: Red-Purple Group 60A.

*Stigmas*.—Color: Near White Group 155C.

Plant:

*Form*.—Bush, dwarf.

*Growth*.—Very vigorous, upright, branching. In a garden at maturity, height is 28 inches, width is 28 inches.

Foliage: Number of leaflets on normal mid-stem leaves: Five.

*Size*.—Small, about 3½ inches long×2 inches wide.

*Quantity*.—Abundant.

*Color*.—New foliage: Upper and lower surfaces: Near Yellow-Green Group 144A and Greyed-Red Group 178B on leaf margins. Old foliage: Upper surfaces: Near Green Group 137A. Lower surfaces: Green Group 137C.

Leaflets:

*Shape*.—Pointed oval.

*Texture*.—Glossy, smooth.

*Edge*.—Serrated.

*Serration*.—Double.

*Petiole rachis*.—Color: Green Group 137C and Greyed-Purple Group 187A.

*Petiole underside*.—Rough, with prickles.

*Stipules*.—Medium (about ½ inch), Serrated.

*Disease resistance*.—Resistant to mildew; susceptible to blackspot and rust under normal growing conditions.

Wood:

*New wood*.—Color: Yellow-Green Group 146B. Bark: Smooth.

*Old wood*.—Color: Near Green Group 137B. Bark: Smooth.

Prickles:

*Quantity*.—On main canes from base: Few. On laterals from main canes: Few.

*Form*.—Short (about ¼ inch long), straight.

*Color when young*.—Near Greyed-Yellow Group 161D.

*Color when mature*.—Near Greyed-Orange Group 165B.

Small prickles:

*Quantity*.—On main stalks: None. On laterals: None.

I claim:

1. A new and distinct variety of rose plant of the miniature rose class, substantially as herein shown and described, characterized particularly by it's bright orange to orange-red color; pointed ovoid bud; small, two-inch flowers; and dark green, glossy, powdery mildew resistant foliage.

* * * * *

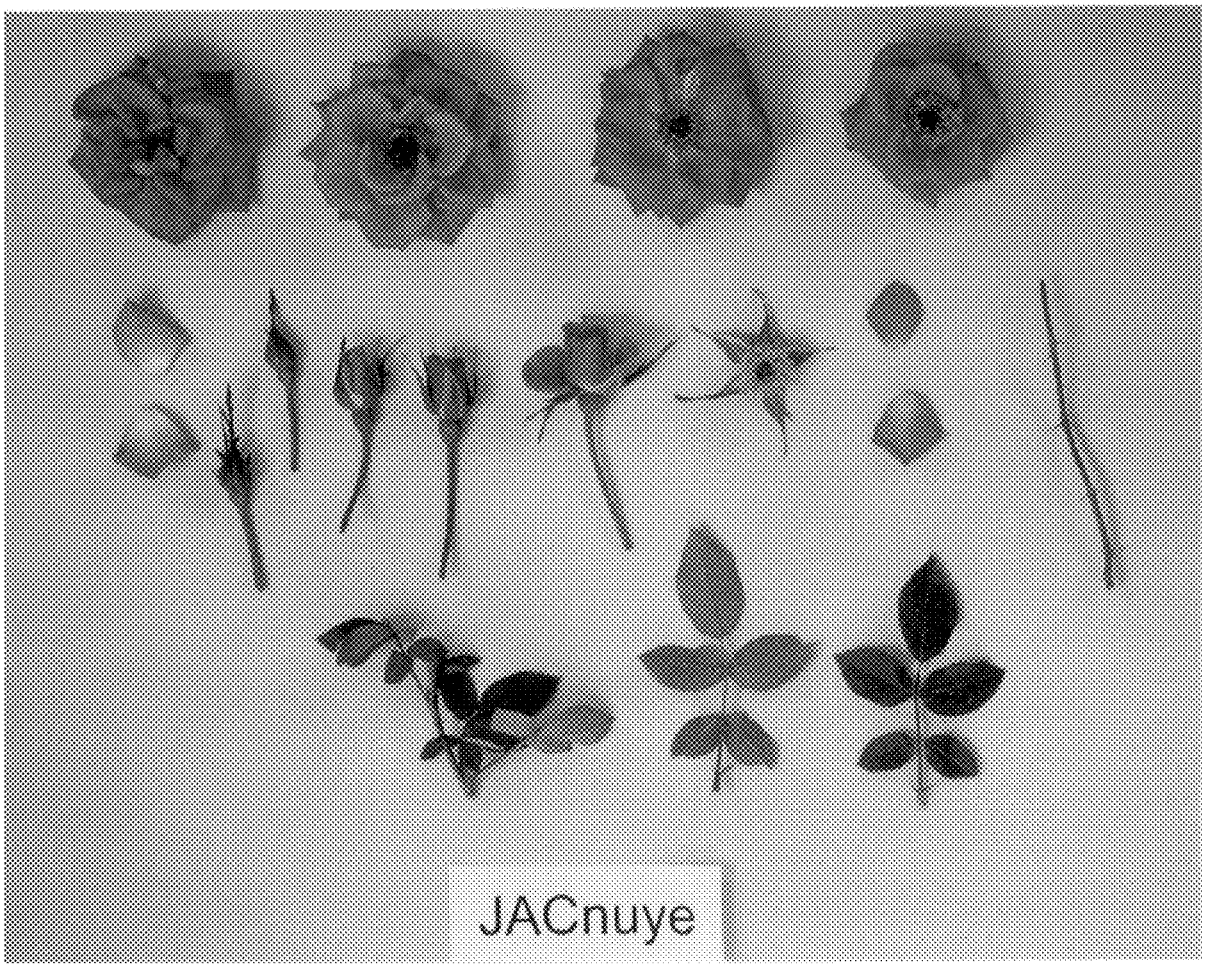
JACnuye